(12) United States Patent
Pandey et al.

(10) Patent No.: US 11,339,145 B2
(45) Date of Patent: *May 24, 2022

(54) SYNTHESIS OF CERDULATINIB

(71) Applicant: Alexion Pharmaceuticals, Inc., Boston, MA (US)

(72) Inventors: Anjali Pandey, Fremont, CA (US); Arvinder Sran, Fremont, CA (US); Ying Chen, Thousand Oaks, CA (US); Daniele Poggiali, Lugano (CH); Tiziano Fumagalli, Lipomo (IT)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/076,356

(22) Filed: Oct. 21, 2020

(65) Prior Publication Data

US 2021/0147392 A1 May 20, 2021

Related U.S. Application Data

(63) Continuation of application No. 16/402,880, filed on May 3, 2019, now Pat. No. 10,851,087.

(60) Provisional application No. 62/822,714, filed on Mar. 22, 2019, provisional application No. 62/667,235, filed on May 4, 2018.

(51) Int. Cl.
*C07D 239/42* (2006.01)
*C07D 403/12* (2006.01)
*C07D 239/47* (2006.01)
*C07D 239/48* (2006.01)

(52) U.S. Cl.
CPC ......... *C07D 403/12* (2013.01); *C07D 239/42* (2013.01); *C07D 239/47* (2013.01); *C07D 239/48* (2013.01)

(58) Field of Classification Search
CPC ... C07D 239/42; C07D 239/47; C07D 239/48
USPC ........................................................ 544/317
See application file for complete search history.

(56) References Cited

U.S. PATENT DOCUMENTS

| | | | |
|---|---|---|---|
| 4,673,747 A | 6/1987 | Nohara et al. | |
| 5,760,032 A | 6/1998 | Kitajima et al. | |
| 6,627,626 B2 | 9/2003 | Minich et al. | |
| 7,449,456 B2 | 11/2008 | Nagashima et al. | |
| 8,012,959 B2 | 9/2011 | Nagashima et al. | |
| 8,138,339 B2 | 3/2012 | Bauer et al. | |
| 8,501,944 B2 | 8/2013 | Bauer et al. | |
| 8,937,070 B2 | 1/2015 | Bauer et al. | |
| 9,868,729 B2 | 1/2018 | Bauer et al. | |
| 10,533,001 B2 | 1/2020 | Bauer et al. | |
| 10,851,087 B2 * | 12/2020 | Pandey | C07D 403/12 |
| 10,865,198 B2 * | 12/2020 | Pandey | C07D 403/12 |
| 2013/0237493 A1 | 9/2013 | Sinha et al. | |
| 2015/0259328 A1 | 9/2015 | Bauer et al. | |
| 2017/0042896 A1 | 2/2017 | Coffey et al. | |
| 2018/0147203 A1 | 5/2018 | Pandey et al. | |
| 2018/0353506 A1 | 12/2018 | Coffey et al. | |
| 2019/0337930 A1 | 11/2019 | Pandey et al. | |
| 2020/0031804 A1 | 1/2020 | Pandey et al. | |
| 2020/0061060 A1 | 2/2020 | Coffey et al. | |

FOREIGN PATENT DOCUMENTS

| | | |
|---|---|---|
| WO | WO 2009/145856 | 12/2009 |
| WO | WO 2011/068898 | 6/2011 |
| WO | WO 2014/058921 | 4/2014 |

OTHER PUBLICATIONS

International Search Report and Written Opinion for PCT/US2019/030635 dated Aug. 20, 2019, 16 pages.

* cited by examiner

*Primary Examiner* — Deepak R Rao
(74) *Attorney, Agent, or Firm* — Sheppard Mullin Richter & Hampton LLP

(57) ABSTRACT

The present disclosure provides processes for the preparation of cerdulatinib, which is of formula I:

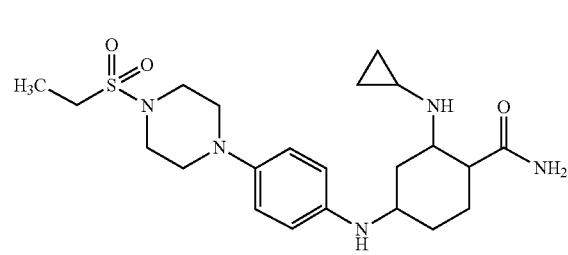

or a salt thereof. The disclosure also provides intermediates and processes for the preparation of the intermediates useful in the preparation of cerdulatinib or a salt thereof.

15 Claims, No Drawings

SYNTHESIS OF CERDULATINIB

CROSS-REFERENCE TO RELATED APPLICATIONS

This application is a continuation of U.S. application Ser. No. 16/402,880, filed on May 3, 2019, which claims priority to U.S. Application Nos. 62/667,235, filed May 4, 2018, and 62/822,714, filed Mar. 22, 2019, each of which is hereby incorporated by reference in their entirety.

FIELD

The present disclosure relates generally to the field of organic synthetic processes for the preparation of cerdulatinib and synthetic intermediates useful in the processes.

BACKGROUND

Cerdulatinib is a small molecule, ATP-competitive, reversible inhibitor of both SYK and JAK family members useful in treating a variety of diseases, including cancers, and is described in U.S. Pat. Nos. 8,138,339 and 8,501,944, the disclosures of which are incorporated herein by reference in their entirety. Cerdulatinib has a chemical name of 4-(cyclopropylamino)-2-(4-(4-(ethylsulfonyl)piperazin-1-yl)phenylamino)pyrimidine-5-carboxamide or 4-(cyclopropylamino)-2-({4-[4 (ethanesulfonyl)piperazin-1-yl]phenyl}amino)pyrimidine-5-carboxamide, and the structure of formula I:

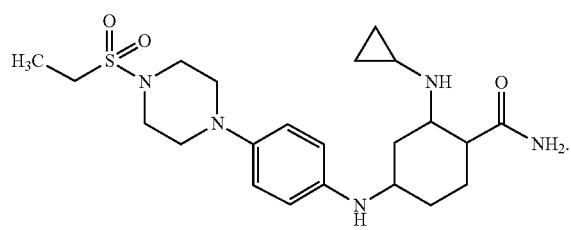

I

SUMMARY

The present disclosure provides processes and intermediates for preparing cerdulatinib or a salt thereof.

In some embodiments, this disclosure provides a process for preparing cerdulatinib, which is of formula I:

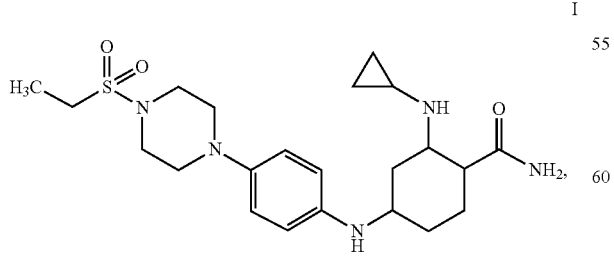

I or a salt thereof, the process comprises contacting Compound A or a salt thereof with Compound B or a salt thereof under conditions to form cerdulatinib or a salt thereof:

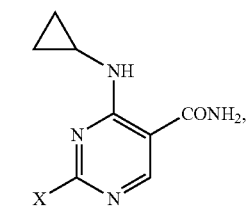

A

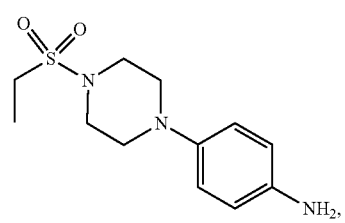

B wherein X is selected from the group consisting of Cl, Br, $CH_3S(O)-$ and $CH_3S(O)_2-$.

In some embodiments, provided is a two-step, one-pot process for preparing cerdulatinib or a salt thereof, comprising
(1) contacting Compound C

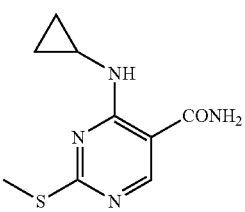

C or a salt thereof with an oxidizing agent or a salt thereof to form Compound A-2 and/or A-3:

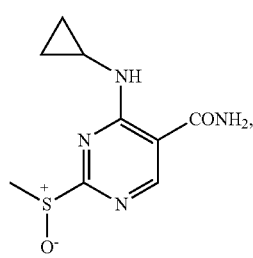

A-2

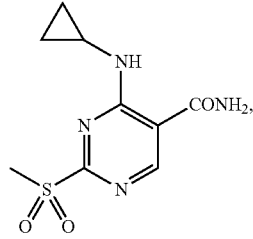

A-3 or a salt thereof, and
(2) contacting Compound A-2 and/or A-3 or a salt thereof with Compound B:

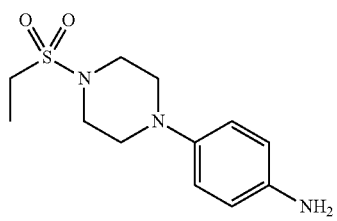

or a salt thereof to form cerdulatinib or a salt thereof, wherein steps (1) and (2) are conducted in one reactor without isolation of intermediates Compound A-2 and/or A-3.

In some embodiments, provided is a three-step, one-pot process for preparing cerdulatinib or a salt thereof, comprising (1) contacting ammonia or a salt thereof with Compound F:

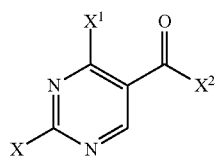

or a salt thereof to form Compound E:

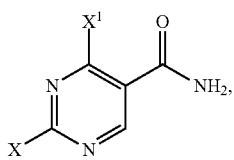

or a salt thereof;

(2) contacting Compound E or a salt thereof with cyclopropylamine or a salt thereof to form Compound A:

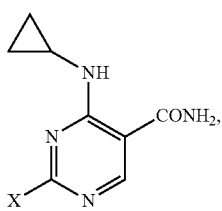

or a salt thereof, and (3) contacting Compound A or a salt thereof with Compound B:

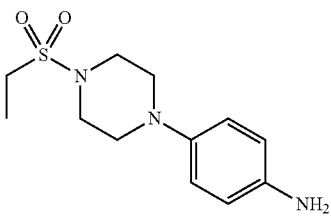

or a salt thereof to form cerdulatinib or a salt thereof, wherein X is selected from the group consisting of Cl, Br, $CH_3S(O)$— and $CH_3S(O)_2$—, $X^1$ and $X^2$ are independently a leaving group, and all of steps (1)-(3) are conducted in one reactor without isolation of intermediates.

In some embodiments, the process further comprises contacting cerdulatinib with an acid to form a pharmaceutically acceptable salt of cerdulatinib.

In some embodiments, provided is a process for preparing cerdulatinib HCl salt comprising contacting cerdulatinib with hydrochloric acid in a solvent comprising dimethyl sulfoxide and ethanol form cerdulatinib HCl salt.

In some embodiments, provided herein is a compound of Formula A:

or a salt thereof, wherein X is selected from the group consisting of Cl, Br, $CH_3S(O)$— and $CH_3S(O)_2$—.

More specific embodiments are described below.

DETAILED DESCRIPTION

Definitions

As used herein the following definitions apply unless clearly indicated otherwise:

As used herein and in the appended claims, the singular forms "a", "an", and "the" include plural referents unless the context clearly dictates otherwise. Thus, for example, reference to "a process" includes a plurality of processes.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "alkyl" refers to monovalent saturated aliphatic hydrocarbyl groups. In some embodiments, alkyl has from 1 to 6 carbon atoms ($C_{1-6}$ alkyl). This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), and t-butyl (($CH_3)_3C$—).

As used herein, the term "solvent" refers to a liquid that dissolves a solid, liquid, or gaseous solute to form a solution. Common solvents are well known in the art and include but are not limited to, water; saturated aliphatic hydrocarbons, such as pentane, hexane, heptane, and other light petroleum; aromatic hydrocarbons, such as benzene, toluene, xylene, etc.; halogenated hydrocarbons, such as dichloromethane, chloroform, carbon tetrachloride, etc.; aliphatic alcohols, such as methanol, ethanol, propanol, etc.; ethers, such as diethyl ether, dipropyl ether, dibutyl ether, tetrahydrofuran, dioxane, etc.; ketones, such as acetone, ethyl methyl ketone, etc.; esters, such as methyl acetate, ethyl acetate, etc.; nitrogen-containing solvents, such as dimethylacetamide, formamide, N,N-dimethylformamide, acetonitrile, pyridine, N-methylpyrrolidone, quinoline, nitrobenzene, etc.; sulfur-containing solvents, such as carbon disulfide, dimethyl sulfoxide, sulfolane, etc.; phosphorus-containing solvents, such as hexamethylphosphoric triamide, etc. The term solvent includes a combination of two or more solvents unless clearly indicated otherwise. A particular choice of a suitable solvent will depend on many factors, including the nature of the solvent and the solute to be dissolved and the intended purpose, for example, what chemical reactions will occur in the solution, and is generally known in the art.

As used herein, the term "contacting" refers to bringing two or more chemical molecules to close proximity so that a chemical reaction between the two or more chemical molecules can occur. For example, contacting may comprise mixing and optionally continuously mixing the chemicals. Contacting may be done by fully or partially dissolving or suspending two or more chemicals in one or more solvents, mixing of a chemical in a solvent with another chemical in solid and/or gas phase or being attached on a solid support, such as a resin, or mixing two or more chemicals in gas or solid phase and/or on a solid support, that are generally known to those skilled in the art.

As used herein, the term "leaving group" refers to an atom (or a group of atoms) that is capable of being displaced as stable species taking with it the bonding electrons. Examples of leaving group including —Cl, —Br, —I, tosyl (-Ts or -OTs), methanesulfonyl (—$SO_2CH_3$), —$SOCH_3$, etc.

All atoms designated within a formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{18}F$, $^{19}F$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

The compounds described herein include any tautomeric forms although the formula of only one of the tautomeric forms of a given compound may be provided herein.

As used herein, the term "salt" refers to acid addition salts and basic addition salts. Examples acid addition salts include those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid. Basic addition salts include those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, Pa., Vol. 2, p. 1457, 1995. Salts include pharmaceutically acceptable salts that do not have properties that would cause a reasonably prudent medical practitioner to avoid administration of the material to a patient, taking into consideration the disease or conditions to be treated and the respective route of administration.

In addition, abbreviations as used herein have respective meanings as follows:

| | |
|---|---|
| AcOH | acetic acid |
| DIPEA | diisopropylethylamine |
| DMF | dimethylformamide |
| DMSO | dimethylsulfoxide |
| eq or equiv. | equivalent |
| EtOH | ethanol |
| EtOH abs. | absolute ethanol |
| GC-FID | gas chromatography - flame ionization detector |
| gm or g | gram |
| h or hr | hour |
| HCl | hydrochloric acid |
| HPLC | high pressure liquid chromatography |
| IPC | in-process control |
| i-PrOH or IPA | isopropanol |
| KF | Karl Fischer test |
| kg | kilogram |
| L | liter |
| M | molarity |
| mCPBA | 3-chloro per-benzoic acid or meta-chloroperoxybenzoic |
| MeOH | methanol |
| MeTHF | 2-methyltetrahydrofuran |
| mL | milliliter |
| ML | mother liquors |
| MTBE | methyl tert-butyl ether |
| N | Normal |
| NaHCO$_3$ | sodium bicarbonate |
| NMP | N-methyl pyrrolidone |
| NaOEt | sodium ethoxide |
| o.d.b. | on dried bases |
| o.n. | overnight |
| PGE | crude dry product |
| PGU | crude wet product |
| TEA | triethylamine |
| THF | tetrahydrofuran |
| tosyl or Ts | para-toluenesulfonyl |
| vol | volume |
| w/w | weight/weight |

Processes

Provided herein are processes for preparing cerdulatinib or a pharmaceutically acceptable salt thereof. In some embodiments, the processes are suitable for large scale manufacturing of cerdulatinib or a pharmaceutically acceptable salt thereof. In some embodiments, the processes are adaptable to different scales, with decreased production costs, and prepare cerdulatinib or a pharmaceutically acceptable salt thereof in high yield and high purity. In some embodiments, the processes are capable of preparing at least 1 kg of cerdulatinib or a pharmaceutically acceptable salt thereof in one batch. In some embodiments, the processes are capable of preparing at least 5 kg of cerdulatinib or a pharmaceutically acceptable salt thereof in one batch. In some embodiments, the processes are capable of preparing at least 10 kg of cerdulatinib or a pharmaceutically acceptable salt thereof in one batch.

In some embodiments, provided is a process for preparing cerdulatinib, which is of formula I:

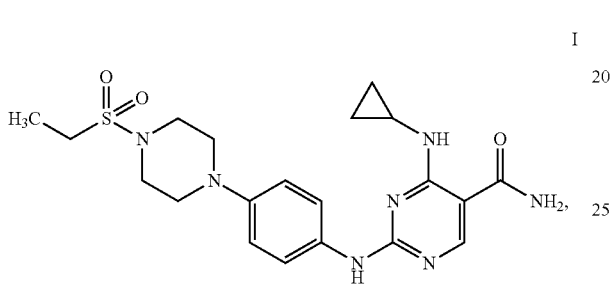

or a salt thereof, the process comprises contacting Compound A or a salt thereof with Compound B or a salt thereof under conditions to form cerdulatinib or a salt thereof:

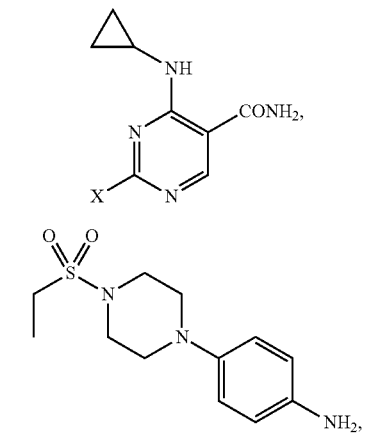

wherein X is selected from the group consisting of Cl, Br, $CH_3S(O)$— and $CH_3S(O)_2$—.

In some embodiments, Compound A is selected from

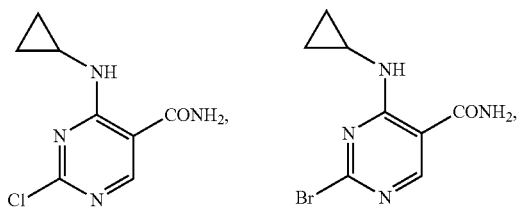

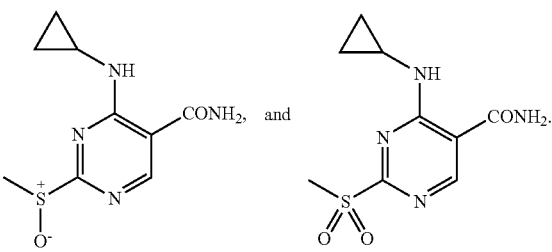

In some embodiments, Compound A or a salt thereof is prepared by a process comprising contacting Compound E

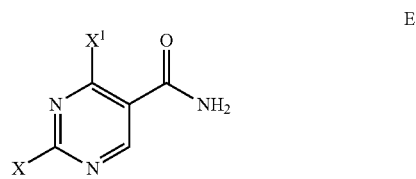

or a salt thereof with cyclopropylamine or a salt thereof under conditions to form Compound A or a salt thereof, wherein $X^1$ is a leaving group.

In some embodiments, Compound E or a salt thereof is prepared by a process comprising contacting Compound F

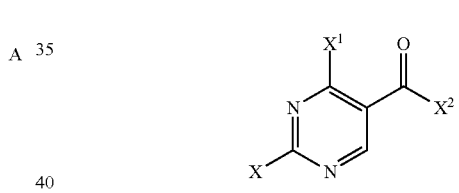

or a salt thereof with ammonia or a salt thereof under conditions to form Compound E or a salt thereof, wherein $X^2$ is a leaving group.

In some embodiments, $X^1$ is Cl. In some embodiments, $X^2$ is Cl, Br or —OR, wherein R is H, or alkyl, such as methyl or ethyl. In some embodiments, X, $X^1$ and $X^2$ are the same. In some embodiments, X, $X^1$ and $X^2$ are Cl. In some embodiments, X, $X^1$ and $X^2$ are different.

In some embodiments, Compound A is Compound A-1:

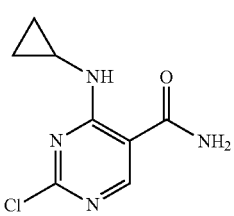

or a salt thereof.

In some embodiments, Compound A-1 or a salt thereof is prepared by a process comprising contacting Compound E-1

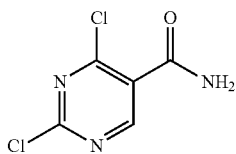

or a salt thereof with cyclopropylamine or a salt thereof under conditions to form Compound A-1 or a salt thereof.

In some embodiments, Compound E-1 or a salt thereof is prepared by a process comprising contacting Compound F-1

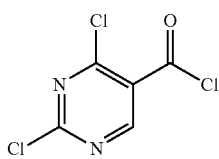

or a salt thereof with ammonia or a salt thereof under conditions to form Compound E-1 or a salt thereof.

In some embodiments, provided is a two-step, one-pot process for preparing cerdulatinib or a salt thereof, comprising
(1) contacting Compound E

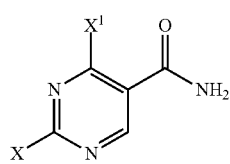

or a salt thereof with cyclopropylamine or a salt thereof to form Compound A:

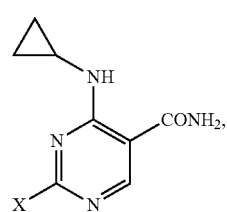

or a salt thereof, and
(2) contacting Compound A or a salt thereof with Compound B:

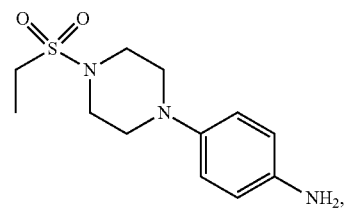

or a salt thereof, to form cerdulatinib or a salt thereof, wherein X is selected from the group consisting of Cl, Br, $CH_3S(O)$— and $CH_3S(O)_2$—, $X^1$ is a leaving group, and steps (1) and (2) are conducted in one reactor without isolation of intermediate Compound A.

In some embodiments, provided is a three-step, one-pot process for preparing cerdulatinib or a salt thereof, comprising steps (1) contacting Compound F or a salt thereof with ammonia or a salt thereof to form Compound E or a salt thereof, (2) contacting Compound E or a salt thereof with cyclopropylamine or a salt thereof to form Compound A or a salt thereof, and (3) contacting Compound A or a salt thereof with Compound B or a salt thereof to form cerdulatinib or a salt thereof, wherein all of steps (1)-(3) are conducted in one reactor without isolation of intermediates.

In some embodiments, the three-step, one-pot process comprises steps (1) contacting Compound F-1:

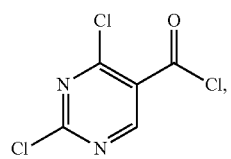

or a salt thereof, with ammonia or a salt thereof to form Compound E-1:

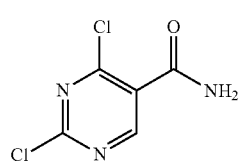

or a salt thereof,
(2) contacting Compound E-1 or a salt thereof with cyclopropylamine or a salt thereof to form Compound A-1:

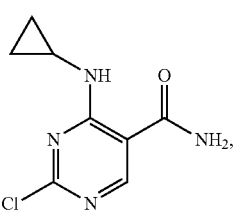

or a salt thereof, and (3) contacting Compound A-1 or a salt thereof with Compound B:

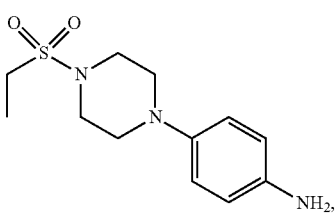

or a salt thereof, to form cerdulatinib or a salt thereof, wherein all of steps (1)-(3) are conducted in one reactor without isolation of intermediates.

In the one-pot process, three nucleophilic substitution reactions occur sequentially in the same reactor wherein in the first two steps a single leaving group is selectively replaced with an amino compound, to form desired intermediates with high purities and minimum by-products, such that cerdulatinib can be prepared in the third step in high purity and yield without isolation of the intermediates.

In some embodiments, the molar ratio of ammonia or a salt thereof to Compound F-1 or a salt thereof is between about 1:1 to about 2.3:1. In some embodiments, the molar ratio of ammonia or a salt thereof to Compound F-1 or a salt thereof is between about 1.7:1 to about 2.3:1. In some embodiments, the molar ratio of ammonia or a salt thereof to Compound F-1 or a salt thereof is between about 1.8:1 to about 2.2:1. In some embodiments, the molar ratio of ammonia or a salt thereof to Compound F-1 or a salt thereof is between about 1.9:1 to about 2.0:1.

In some embodiments, the contacting of ammonia or a salt thereof and Compound F-1 or a salt thereof is in a solvent. In some embodiments, the solvent comprises NMP, MeTHF or THF. In some embodiments, the solvent comprises MeTHF. In some embodiments, the ammonia is bubbled to the solution of Compound F-1 or a salt thereof in the solvent. In some embodiments, the ammonia or a salt thereof is added in a solution such as an NMP or THF solution. In some embodiments, the contacting of ammonia or a salt thereof and Compound F-1 or a salt thereof is in the presence of a base, such as diisopropylethylamine.

In some embodiments, the contacting of ammonia or a salt thereof and Compound F-1 or a salt thereof is at a temperature of about −20° C. to about 0° C. In some embodiments, the contacting of ammonia or a salt thereof and Compound F-1 or a salt thereof is at a temperature of about −15° C. to about −5° C.

In some embodiments, the conversion rate of Compound F-1 or a salt thereof to Compound E-1 or a salt thereof is at least about 99%. In some embodiments, the conversion rate of Compound F-1 or a salt thereof to Compound E-1 or a salt thereof is at least about 99.4%.

In some embodiments, the molar ratio of cyclopropylamine or a salt thereof to Compound E-1 or a salt thereof is between about 1:1 to about 2:1. In some embodiments, the molar ratio of cyclopropylamine or a salt thereof to Compound E-1 or a salt thereof is about 2:1. In some embodiments, the molar ratio of cyclopropylamine or a salt thereof to Compound E-1 or a salt thereof is between about 1:1 to about 1.2:1 and a base, such as triethylamine or diisopropylethylamine, is also present. In some embodiments, the molar ratio of the base to Compound E-1 or a salt thereof is between about 1:1 to about 1.5:1. In some embodiments, the molar ratio of the base to Compound E-1 or a salt thereof is between about 1:1 to about 1.2:1.

In some embodiments, the contacting of cyclopropylamine or a salt thereof and Compound E-1 or a salt thereof is in a solvent. In some embodiments, the solvent comprises THF or MeTHF.

In some embodiments, the contacting of cyclopropylamine or a salt thereof and Compound E-1 or a salt thereof is at a temperature of about −20° C. to about 0° C. In some embodiments, the contacting of cyclopropylamine or a salt thereof and Compound E-1 or a salt thereof is at a temperature of about −15° C. to about 0° C., such as about −15° C., about −5° C. or about 0° C.

In some embodiments, no more than 0.5% of Compound E-1 or a salt thereof remains after the contacting of cyclopropylamine or a salt thereof with Compound E-1 or a salt thereof. In some embodiments, no more than 0.2% of Compound E-1 or a salt thereof remains after the contacting of cyclopropylamine or a salt thereof with Compound E-1 or a salt thereof.

In some embodiments, the mixture comprising Compound A-1 or a salt thereof resulting from the contacting of cyclopropylamine or a salt thereof with Compound E-1 or a salt thereof is washed with water or an aqueous solution to obtain a solution comprising Compound A-1 or a salt thereof. In some embodiments, the solvent of solution comprising Compound A-1 or a salt thereof, such as THF or MeTHF, is replaced with a different solvent, such as NMP.

In some embodiments, the molar ratio of Compound A-1 or a salt thereof to Compound B or a salt thereof is about 1:1. In some embodiments, the contacting of Compound A-1 or a salt thereof and Compound B or a salt thereof is at a temperature of about 70° C. to about 120° C.

In some embodiments, the contacting of Compound A-1 or a salt thereof and Compound B or a salt thereof is under a neutral condition. In some embodiments, the contacting of Compound A-1 or a salt thereof and Compound B or a salt thereof under a neutral condition is at a temperature of about 70° C. to about 100° C., or about 80° C. to about 90° C.

In some embodiments, the contacting of Compound A-1 or a salt thereof and Compound B or a salt thereof is in a basic condition wherein a base, such as diisopropylethylamine or triethylamine, is added. In some embodiments, the molar ratio of the base to Compound A-1 or a salt thereof or Compound B or a salt thereof is about 1:1. In some embodiments, the contacting of Compound A-1 or a salt thereof and Compound B or a salt thereof under a basic condition is at a temperature of about 100° C. to about 120° C. or about 100° C. to about 105° C.

In some embodiments, the contacting of Compound A-1 or a salt thereof and Compound B or a salt thereof is under an acid condition wherein an acid, such as HCl, is added. In some embodiments, the molar ratio of the acid to Compound A-1 or a salt thereof or Compound B or a salt thereof is about 1.2:1. In some embodiments, the contacting of Compound A-1 or a salt thereof and Compound B or a salt thereof under an acid condition is at a temperature of about 70° C. to about 90° C. or about 80° C.

In some embodiments, a salt of cerdulatinib is prepared by contacting Compound A or a salt thereof and Compound B or a salt thereof under an acid condition or a neutral condition. In some embodiments, the process further comprises converting the salt of cerdulatinib to cerdulatinib free base by adding a base.

In some embodiments, the process further comprises isolating cerdulatinib. In some embodiments, cerdulatinib is isolated by a process comprising precipitation, such as by addition of water, and filtration.

In some embodiments, the three-step, one-pot process prepares cerdulatinib in an overall yield of at least about 80%, or at least about 85%. In some embodiments, the three-step, one-pot process prepares cerdulatinib with purity of at least about 90%, or at least about 95%.

In some embodiments, Compound F-1 or a salt thereof is prepared by a process comprising contacting $POCl_5$ with Compound G:

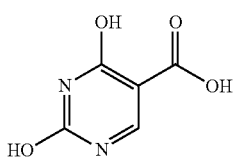

or a salt thereof.

In some embodiments, the molar ratio of POCl$_5$ to Compound G or a salt thereof is between about 2.5:1 to about 3.5:1. In some embodiments, the molar ratio of POCl$_5$ to Compound G or a salt thereof is between about 2.8:1 to about 3.2:1. In some embodiments, the molar ratio of POCl$_5$ to the Compound G or a salt thereof is between about 2.9:1 to about 3.1:1.

In some embodiments, the contacting of POCl$_5$ and Compound G or a salt thereof is in a solvent. In some embodiments, the solvent is POCl$_3$.

In some embodiments, the contacting of POCl$_5$ and Compound G or a salt thereof is under reflux conditions, such as at about 70° C. to about 120° C. In some embodiments, the contacting of POCl$_5$ and Compound G or a salt thereof is under reflux conditions, such as at about 80° C. to about 105° C. In some embodiments, the contacting of POCl$_5$ and Compound G or a salt thereof is for a period of time sufficient for reaction to complete, such as about 2 hours to about 30 hours, or about 2 hours to about 5 hours.

In some embodiments, Compound F-1 or a salt thereof is isolated by distillation to remove the solvent. In some embodiments, the yield of Compound F-1 or a salt thereof is at least about 60%. In some embodiments, the yield of Compound F-1 or a salt thereof is at least about 70%. In some embodiments, the purity of Compound F-1 or a salt thereof is at least about 90%. In some embodiments, the purity of Compound F-1 or a salt thereof is at least about 95%.

In some embodiments, Compound A is Compound A-2 or Compound A-3 or a mixture thereof,

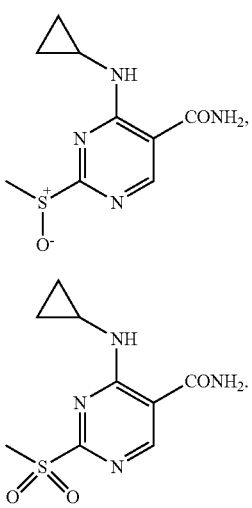

In some embodiments, Compound A is a mixture of Compound A-2 and Compound A-3. In some embodiments, Compound A is a mixture of about 55%-65% Compound A-2 and 35%-45% Compound A-3. In some embodiments, Compound A is a mixture of about 60% Compound A-2 and 40% Compound A-3.

In some embodiments, Compound A-2 or Compound A-3 or a salt thereof, or a mixture thereof, is prepared by a process comprising contacting an oxidizing agent, such as meta-chloroperoxybenzoic acid, with Compound C:

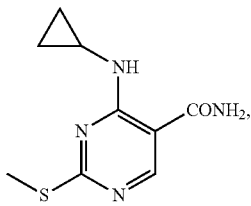

or a salt thereof.

In some embodiments, Compound A is Compound A-2 or Compound A-3 or a mixture thereof, and cerdulatinib or a salt thereof is prepared by a process comprising contacting Compound A-2 or Compound A-3 or a salt thereof or a mixture thereof, with Compound B or a salt thereof.

In some embodiments, provided is a two-step, one-pot process for preparing cerdulatinib comprising step (1) contacting Compound C or a salt thereof with an oxidizing agent, such as meta-chloroperoxybenzoic acid (mCPBA) or a salt thereof, to form Compound A-2 or Compound A-3 or a salt thereof or a mixture thereof, and (2) contacting Compound A-2 or Compound A-3 or a salt thereof, or a mixture thereof, with Compound B or a salt thereof to form cerdulatinib or a salt thereof.

In some embodiments, the molar ratio of Compound B or a salt thereof to the total of Compounds A-2 and A-3 or a salt thereof, or a mixture thereof is about 1:1 to 1.1:1. In some embodiments, the molar ratio of Compound B or a salt thereof to the total of Compounds A-2 and A-3 or a salt thereof, or a mixture thereof is about 1.05:1.

In some embodiments, the contacting of Compound A or a salt thereof, for example Compound A-2 or Compound A-3 or a salt thereof or a mixture thereof, with Compound B or a salt thereof is at a temperature of about 35° C. to about 45° C., or about 45° C. to about 55° C., or about 55° C. to about 65° C. In some embodiments, the temperature is about 40° C. In some embodiments, the temperature is about 45° C. In some embodiments, the temperature is about 50° C. In some embodiments, the temperature is about 55° C. In some embodiments, the temperature is about 60° C. In some embodiments, the contacting of Compound A or a salt thereof, for example Compound A-2 or Compound A-3 or a salt thereof or a mixture thereof, with Compound B or a salt thereof is for about 8 hours to a day. In some embodiments, the contacting of Compound A or a salt thereof, for example Compound A-2 or Compound A-3 or a salt thereof or a mixture thereof, with Compound B or a salt thereof is for about 8 hours to about 24 hours. In some embodiments, the contacting of Compound A or a salt thereof, for example Compound A-2 or Compound A-3 or a salt thereof or a mixture thereof, with Compound B or a salt thereof is for about 16 hours. In some embodiments, the contacting of Compound A or a salt thereof, for example Compound A-2 or Compound A-3 or a salt thereof or a mixture thereof, with Compound B or a salt thereof is for about 22 hours.

In some embodiments, the molar ratio of the oxidizing agent to Compound C or a salt thereof is about 2:1 to about 4:1. In some embodiments, the molar ratio of the oxidizing agent to Compound C or a salt thereof is about 2.5:1 to about 3.5:1. In some embodiments, the molar ratio of the oxidizing agent to Compound C or a salt thereof is about 3:1. In some embodiments, the molar ratio of the oxidizing agent to Compound C or a salt thereof is about 1.1:1 to about 2:1. In some embodiments, the molar ratio of the oxidizing agent to Compound C or a salt thereof is about 1.5:1.

In some embodiments, the contacting of Compound C or a salt thereof with an oxidizing agent is at a temperature of about −10° C. to about 20° C. In some embodiments, the contacting of Compound C or a salt thereof with an oxidizing agent is at a temperature of about −10° C. to about 30° C. In some embodiments, the contacting of Compound C or a salt thereof with an oxidizing agent is at a temperature of about 0° C. to about 10° C. In some embodiments, contacting of Compound C or a salt thereof with an oxidizing agent, and contacting of Compound A or a salt thereof, for example Compound A-2 or Compound A-3 or a salt thereof or a mixture thereof, with Compound B or a salt thereof are in a same solvent, such as NMP. In some embodiments, the contacting of Compound C or a salt thereof with an oxidizing agent is for about 30 minutes to about 2 hours, or about 1 hour. In some embodiments, the contacting of Compound C or a salt thereof with an oxidizing agent is for about 2 hours.

In some embodiments, the mixture of Compound C or a salt thereof and an oxidizing agent is heated to a temperature of about 20° C. to about 30° C. In some embodiments, the mixture of Compound C or a salt thereof and an oxidizing agent is heated to a temperature of about 25° C. In some embodiments, the heating of Compound C or a salt thereof with an oxidizing agent is for about 30 minutes to about 5 hours. In some embodiments, the heating of Compound C or a salt thereof with an oxidizing agent is for about 1.5 hours. In some embodiments, the heating of Compound C or a salt thereof with an oxidizing agent is for about 3 hours. In some embodiments, the heating of Compound C or a salt thereof with an oxidizing agent is for about 4.5 hours.

In some embodiments, the two-step, one-pot process prepares cerdulatinib in an overall yield of at least about 80%. In some embodiments, the two-step, one-pot process prepares cerdulatinib in an overall yield of at least about 85%. In some embodiments, the two-step, one-pot process prepares cerdulatinib with a purity of at least about 85%. In some embodiments, the two-step, one-pot process prepares cerdulatinib with a purity of at least about 90%. In some embodiments, the two-step, one-pot process prepares cerdulatinib with less than about 2% residual Compound C, less than about 1.6% residual Compound C, less than about 1% residual Compound C, or less than about 0.5% residual Compound C.

In some embodiments, Compound C or a salt thereof is prepared by a process comprising contacting formamide or ammonia or a salt thereof with Compound D:

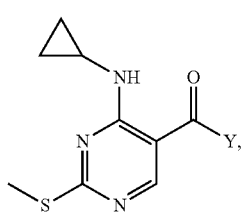

D or a salt thereof, wherein Y is selected from OR, Cl, Br, and other suitable leaving groups, wherein R is H or alkyl, such as methyl or ethyl.

In some embodiments, Compound D is Compound D-1

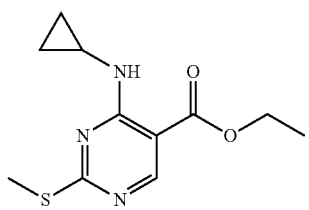

D-1 or a salt thereof.

In some embodiments, Compound C is prepared by a process comprising contacting Compound D-1 or a salt thereof with formamide and sodium ethoxide. In some embodiments, the molar ratio of formamide to Compound D-1 or a salt thereof is about 5:1 to about 20:1. In some embodiments, the molar ratio of formamide to Compound D-1 or a salt thereof is about 5:1 to about 15:1. In some embodiments, the molar ratio of formamide to Compound D-1 or a salt thereof is about 10:1. In some embodiments, the molar ratio of sodium ethoxide to Compound D-1 or a salt thereof is about 1:1 to about 5:1. In some embodiments, the molar ratio of sodium ethoxide to Compound D-1 or a salt thereof is about 3:1. In some embodiments, the process comprises a solvent selected from DMF, NMP, and THF, and a mixture thereof. In some embodiments, the solvent is THF. In some embodiments, the weight ratio of THF to Compound D-1 or a salt thereof is about 1.0 w/w to 3.0 w/w. In some embodiments, the weight ratio of THF to Compound D-1 or a salt thereof is about 2.0 w/w. In some embodiments, the contacting of Compound D-1 or a salt thereof with formamide and sodium ethoxide is for about 2 hours to about 24 hours. In some embodiments, the contacting of Compound D-1 or a salt thereof with formamide and sodium ethoxide is for about 10 to about 24 hours. In some embodiments, the contacting of Compound D-1 or a salt thereof with formamide and sodium ethoxide is for about 20 hours. In some embodiments, the contacting of Compound D-1 or a salt thereof with formamide and sodium ethoxide is at a temperature of about −10° C. to about 20° C. In some embodiments, the contacting of Compound D-1 or a salt thereof with formamide and sodium ethoxide is at a temperature of about 0° C. to about 10° C. In some embodiments, the contacting of Compound D-1 or a salt thereof with formamide and sodium ethoxide is at a temperature of about 5° C. In some embodiments, the process does not comprise forming Compound D-2. In some embodiments, the process does not comprise isolating Compound D-2.

In some embodiments, Compound D-1 is prepared by reacting Compound K:

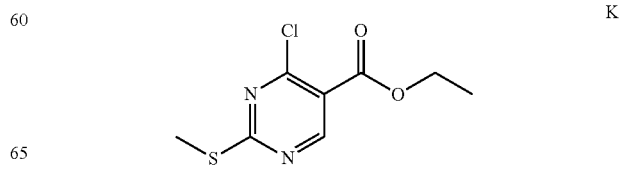

K or a salt thereof with cyclopropylamine or a salt thereof. In some embodiments, purification of Compound D-1 comprises filtration of melted material. In some embodiments of the purification of Compound D-1, the material is melted at about 40° C. to about 70° C., or about 45° C. to about 60° C. In some embodiments of the purification of Compound D-1, the material is melted at about 45° C., about 50° C., about 55° C., about 60° C., about 65° C., or about 70° C. In some embodiments of the preparation of Compound D-1, Compound D-1 is prepared in a purity of at least about 98%, for example, about 98% purity, about 99% purity, or about 99.5% purity.

In some embodiments, Compound D is Compound D-2

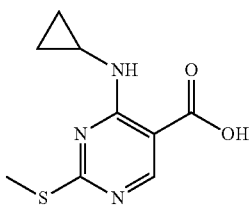

D-2 or a salt thereof.

In some embodiments, Compound C is prepared by a process comprising contacting Compound D-2 or a salt thereof with formamide.

In some embodiments, Compound D-2 is prepared by reacting Compound D-1 or a salt thereof with a hydrolyzing agent. In some embodiment the hydrolyzing agent may be selected from sodium hydroxide, potassium hydroxide, lithium hydroxide, and sodium ethoxide in water.

In some embodiments, Compound B or a salt thereof is prepared by a process comprising reduction of Compound H

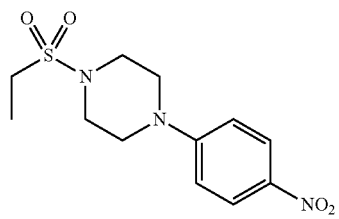

H or a salt thereof.

In some embodiments, the reduction of Compound H or a salt thereof comprises contacting Compound H or a salt thereof with hydrogen gas in the presence of a catalyst, such as palladium on carbon in a solvent, such as methanol or ethanol.

In some embodiments, Compound H or a salt thereof is prepared by a process comprising contacting Compound L or a salt thereof with Compound M or a salt thereof

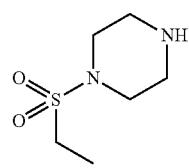

L

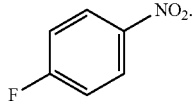

M

In some embodiments, Compound H or a salt thereof is prepared by a process comprising contacting Compound J

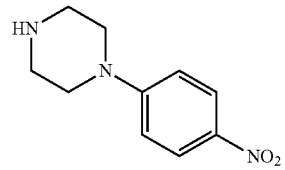

J or a salt thereof with $CH_3CH_2SO_2X^3$ wherein $X^3$ is a leaving group, such as Cl or Br.

In some embodiments, the contacting of Compound J or a salt thereof with $CH_3CH_2SO_2X^3$ is in the presence of a base, such as triethylamine or diisopropylethylamine, in a solvent, such as acetonitrile.

In some embodiments, the processes described herein further comprise contacting cerdulatinib with an acid to form a salt of cerdulatinib. In some embodiments, the salt of cerdulatinib is cerdulatinib HCl salt and the process comprises contacting cerdulatinib with hydrochloric acid. In some embodiments, the contacting of cerdulatinib with hydrochloric acid is in a solvent comprising dimethyl sulfoxide and ethanol. In some embodiments, the contacting is at about 70° C. to about 80° C. or about 75° C. In some embodiments, the process further comprises isolating and purifying cerdulatinib HCl salt. In some embodiments, isolation and purification of cerdulatinib HCl salt comprises stirring cerdulatinib HCl salt in ethanol, filtering and drying.

In some embodiments, provided is a process for preparing cerdulatinib HCl salt comprising contacting cerdulatinib with hydrochloric acid in a solvent comprising dimethyl sulfoxide and ethanol form cerdulatinib HCl salt. In some embodiments, the contacting is at about 60° C. to about 90° C. or about 70° C. to about 80° C. or about 75° C. In some embodiments, the process further comprises isolating and purifying cerdulatinib HCl salt. In some embodiments, isolation and purification of cerdulatinib HCl salt comprises stirring cerdulatinib HCl salt in ethanol, filtering and drying.

Intermediates

In some embodiments, provided herein is a compound of Formula A:

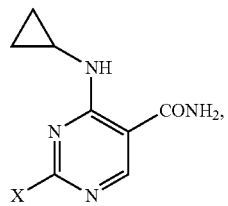

A or a salt thereof, wherein X is selected from the group consisting of Cl, Br, $CH_3S(O)$— and $CH_3S(O)_2$—.

In some embodiments, Compound A is selected from

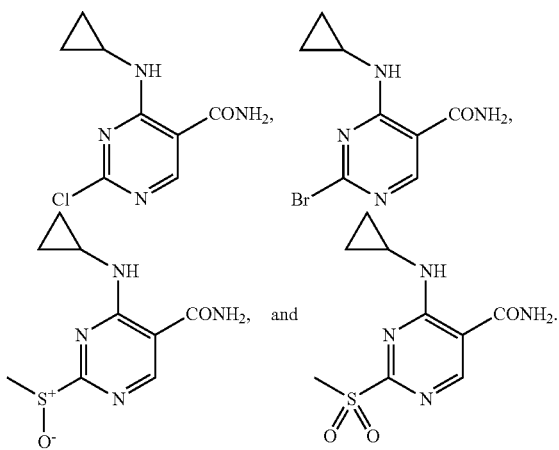

In some embodiments, provided herein is a compound of Formula C or D-1:

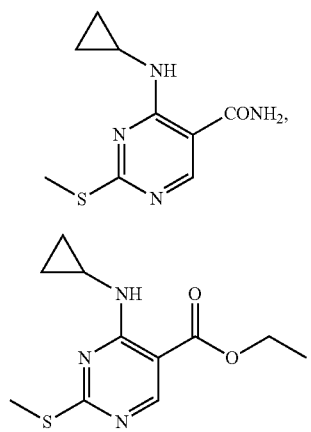

or a salt thereof.

In some embodiments, provided herein is a compound of Formula E or F:

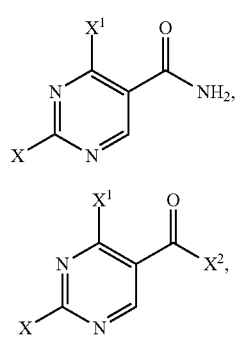

or a salt thereof, wherein X is selected from the group consisting of Cl, Br, CH$_3$S(O)— and CH$_3$S(O)$_2$—, and X$^1$ and X$^2$ are independently a leaving group.

In some embodiments, X$^1$ is Cl. In some embodiments, X$^2$ is Cl, Br or —OR, wherein R is H, or alkyl, such as methyl or ethyl. In some embodiments, X, X$^1$ and X$^2$ are the same. In some embodiments, X, X$^1$ and X$^2$ are Cl. In some embodiments, X, X$^1$ and X$^2$ are different.

In some embodiments, provided herein is a compound of Formula E-1 or F-1:

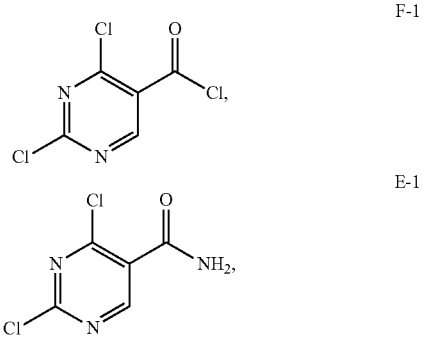

or a salt thereof.

C By-Products

In some embodiments, the processes described herein minimize or eliminate one or more by-products generated during preparation of cerdulatinib.

In some embodiments, the by-product is one or more compounds selected from:

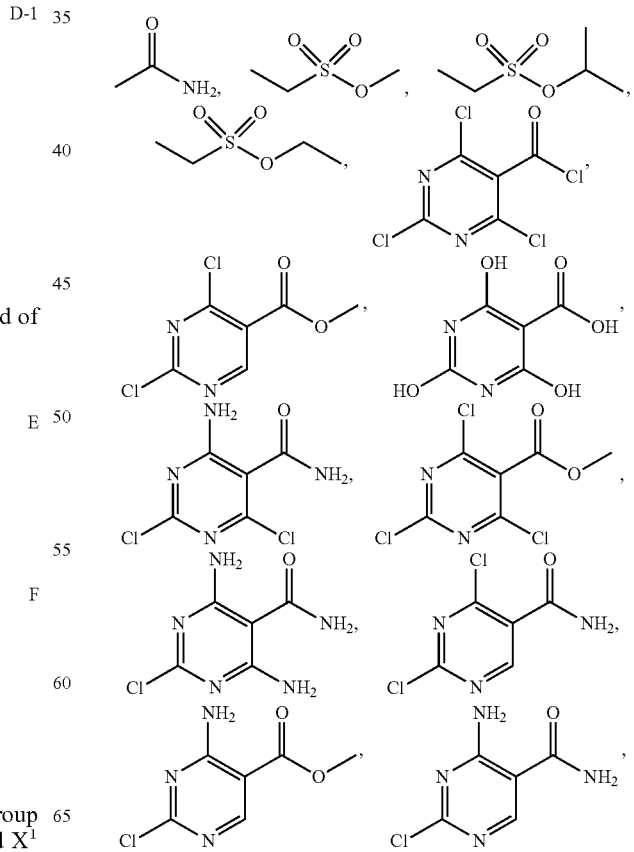

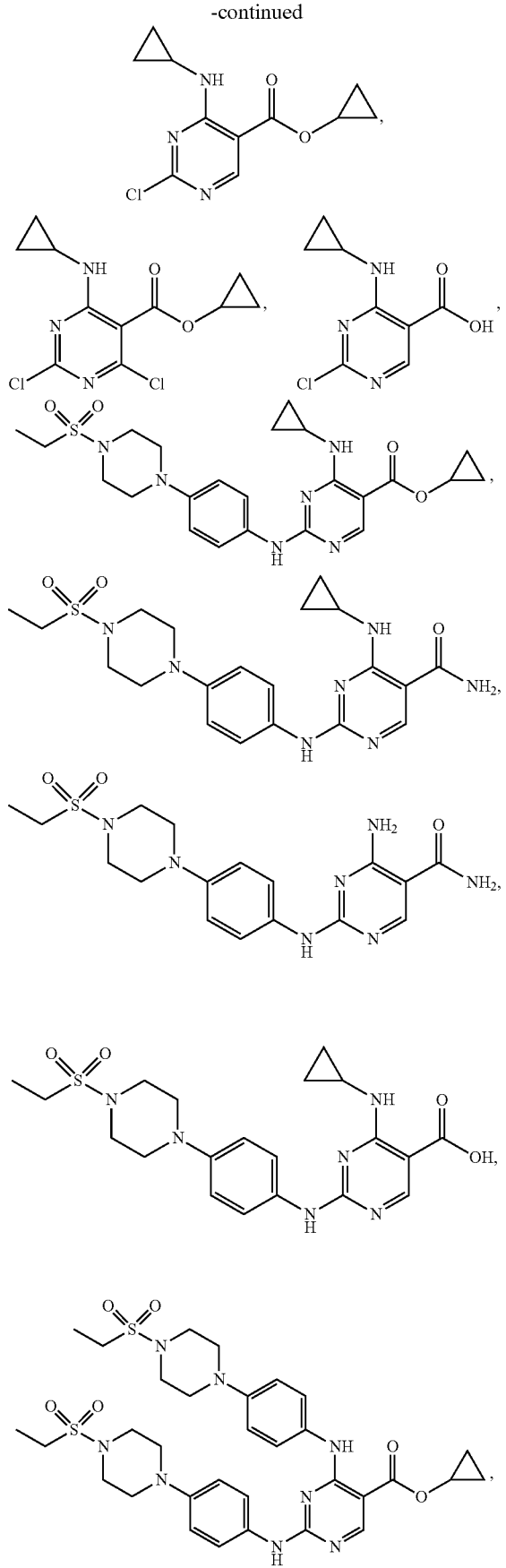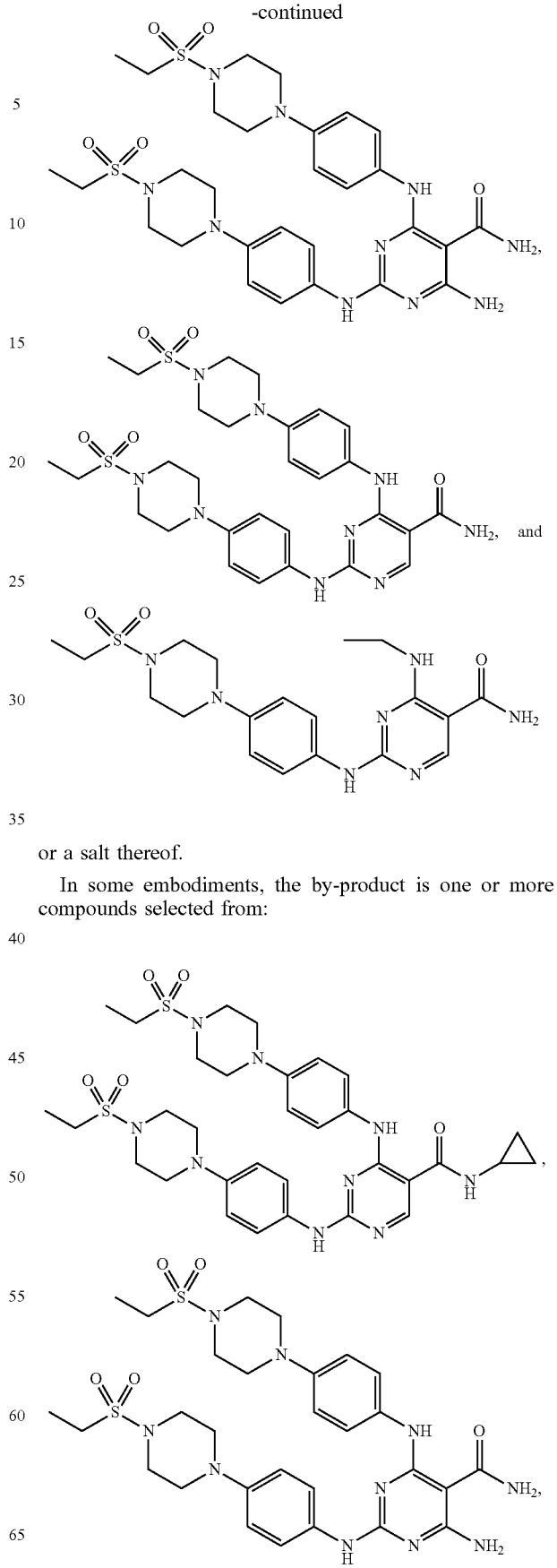
or a salt thereof.
In some embodiments, the by-product is one or more compounds selected from:

-continued

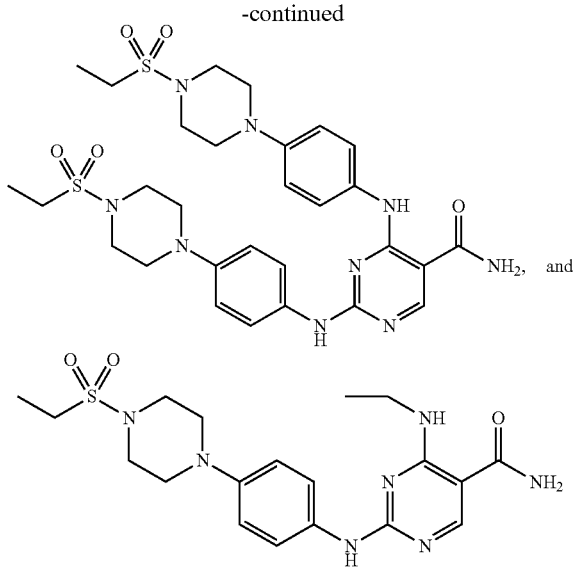

or a salt thereof.

In some embodiments, the one or more by-products, or a salt thereof, is present in less than about 4%, less than about 3%, less than about 2%, less than about 1%, less than about 0.5%, less than about 0.2%, or less than about 0.1% relative to the amount of cerdulatinib or a salt thereof. In some embodiments, the one or more by-products, or a salt thereof, is present in less than about 4% relative to the amount of cerdulatinib or a salt thereof. In some embodiments, the one or more by-products, or a salt thereof, is present in less than about 0.2% relative to the amount of cerdulatinib or a salt thereof. In some embodiments, a process for synthesizing cerdulatinib, or a salt thereof, as provided herein produces the one or more by-products, or a salt thereof, in less than about 4%, less than about 3%, less than about 2%, less than about 1%, less than about 0.5%, less than about 0.2%, or less than about 0.1% relative to the amount of cerdulatinib or a salt thereof.

In some embodiments, a composition comprising at least 96%, at least 97%, at least 98%, at least 99%, at least 99.5%, at least 99.8%, or at least 99.9% cerdulatinib, or a salt thereof, is provided. In some embodiments, a composition is provided comprising at least 96%, at least 97%, at least 98%, at least 99%, at least 99.5%, at least 99.8%, or at least 99.9% cerdulatinib, or a salt thereof, and at least one of the one or more by-products. In some embodiments, the cerdulatinib salt is an HCl salt.

EXAMPLES

Examples related to the present disclosure are described below. In certain cases, alternative techniques can be used. The examples are intended to be illustrative and are not limiting or restrictive to the scope of the disclosure.

Example 1

In this example, cerdulatinib and cerdulatinib HCl salt were prepared according to Scheme 1 in an overall yield of 47.3%.

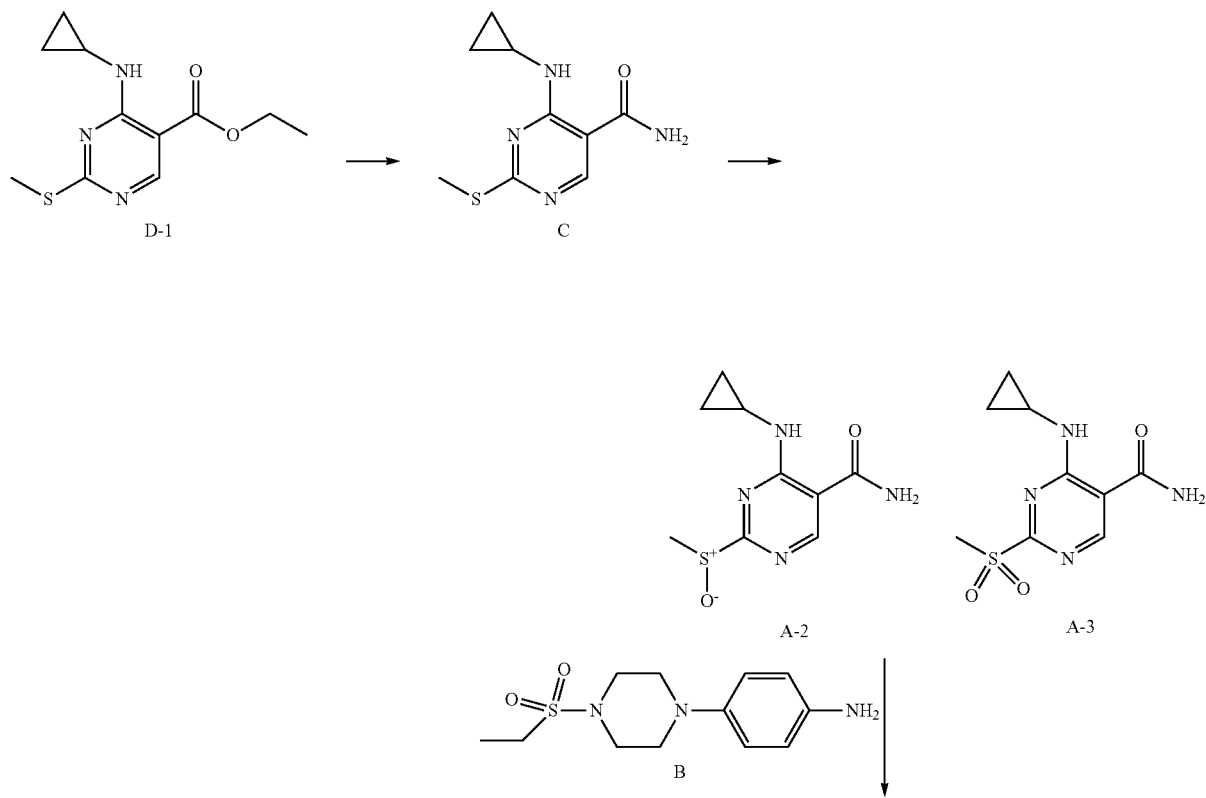

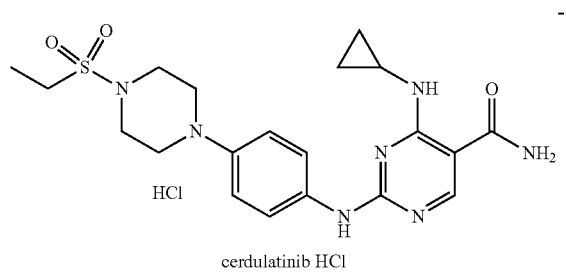

cerdulatinib HCl

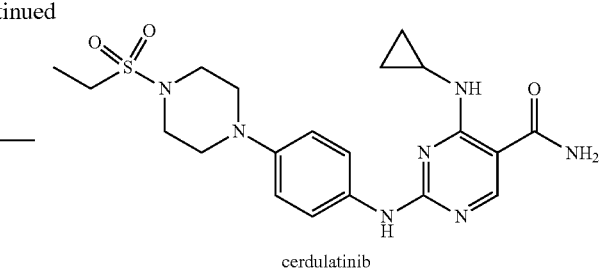

cerdulatinib

Step 1: Conversion of Compound D-1 to Compound C 86.0 Kg of DMF, 76.5 kg of formamide, and 45.5 kg of Compound D-1, were charged in a reactor. To this mixture after having reached an internal temperature of 0-10° C., 84.0 kg of sodium ethoxide 21% were added keeping the internal temperature between 0-10° C. The mixture was warmed up to 50° C. and stirred for 60 minutes. IPC showed that residual content of Compound D-1 was 3.14%. The mixture was cooled to 0° C. and 900 L of water were added, after having finished the water addition, the reaction was cooled down again to −5° C. and it was left stirring for 16 hrs. The mixture was filtered and the filter cake was washed with 50 kg of cold MTBE.

The filter cake (52.95 kg) containing Compound C was forwarded to a dryer. Drying of Compound C PGU (60° C. for 21 hrs and 40 minutes) gave 37.30 kg (92.6% yield) of Compound C PGE. Purity 97.54%.

Step 2: Synthesis of Cerdulatinib

235 Kg of NMP, and 32.1 kg of Compound C PGE were charged to a reactor. The internal temperature was set at between 0-10° C. 72.95 Kg of mCPBA were charged while keeping the temperature under 5° C. The mixture was then warmed up to 25° C. and stirred for 1 hr. IPC showed that residual content of Compound C was 0.00% for oxidative reaction. The mixture was kept stirring at 25° C. for a further hour.

To the above mixture, 40.05 kg of Compound B was added. The internal temperature was set at 40° C. and the mixture was stirred o.n. for 17 hrs and 17 minutes, and then for additional 4 hrs. IPC showed that residual content of Compound A-2+Compound A-3 was 2.05%. The mixture was cooled down to 3° C., and a pre-cooled basic solution of water (642 L) and NaHCO$_3$ (48 kg) was added to the mixture. The mixture was stirred for 1 hr and then water (193 L) was added keeping the internal temperature between 0-10° C. The mixture was stirred for 40 minutes. Solid was isolated by filtration (filter-dryer equipped with 20 μm mesh) keeping squeezing the cake with both N$_2$/vacuum for 51 hrs.

Cerdulatinib PGU (106.9 kg) was then re-charged in the reactor and slurred at 25° C. for 9 hrs with water (1434 L).

Solid was isolated by filtration (filter-dryer equipped with 20 μm mesh cloth) keeping squeezing the cake with both N$_2$/vacuum for 60 hrs.

Wet solid was respectively slurred and squeezing four times more in the filter-dryer using water (877 L).

Solid was then forwarded to the filter-dryer for isolation and drying (43° C. under vacuum for 20 hrs). Cerdulatinib PGE overall yield was 88% (63.76 kg) with purity of 90.84%.

Step 3: Synthesis of Cerdulatinib HCl Salt

252 Kg of DMSO and 56.2 kg of cerdulatinib were charged in the reactor. The mixture was warmed up to 75° C. and stirred till complete dissolution. 664 Kg of EtOH abs. was added and the reaction was stirred for 30 minutes. Keeping the internal temperature in between 70-80° C. (72.9° C.), an acidic solution made by mixing 347 kg of water and 43 kg of HCl 33% w/w was added. The reaction was stirred for further 30 minutes. The mixture was then cooled down to 20° C. and stirred for 19 hrs. Solid was then forwarded to the filter-dryer (20 μm mesh cloth) for isolation. Wet solid was respectively slurred and squeezing twice directly in the filter-dryer using EtOH (1073 L), and then dried (at 35° C. under vacuum for 50 hrs). Cerdulatinib HCl salt yield was 58.4% (35.44 kg) with a purity of 99.41%.

Example 2. Preparation of Cerdulatinib

Step 1: Preparation of Compound F-1

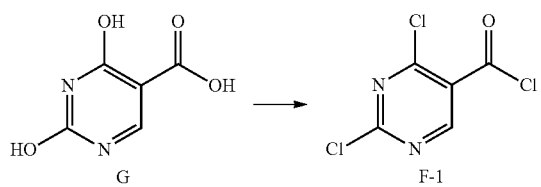

The starting material Compound G was introduced in the reactor with POCl$_3$ and about 3 equivalents of PCl$_5$. In this case POCl$_3$ acted as solvent due to the very low solubility of Compound G in many organic solvents. The reaction temperature was increased from 80° C. to 105° C. in 3 hrs and then left at 105° C. for additional 1-2 hrs. When the reaction completed, POCl$_3$ was distilled. Toluene was added to the residue and distilled in order to reduce the amount of POCl$_3$. Crude Compound F-1 was distilled at around 7-8 mbar, with a jacketed temperature of about 130-135° C. Average yield 72% and average purity 94.9% by GC-FID.

Step 2: Preparation of Cerdulatinib

The strategy adopted for the synthesis of cerdulatinib was a three-step, one-pot process, without any intermediate isolation. As shown in Scheme 2, the three chloride leaving groups present in Compound F-1 were consecutively replaced with the corresponding amines, ammonia, cyclopropylamine, and Compound B. The addition of ammonia and cyclopropylamine was performed at low temperature such as about −15/−5° C. The addition of Compound B was performed at higher temperature such as from 80 to 110° C. At the end of the synthesis, cerdulatinib was precipitated by adding water to the NMP solution. For all steps, the equivalents of all reagents are calculated from the amount of Compound F-1 engaged in step 2.1.

Scheme 2

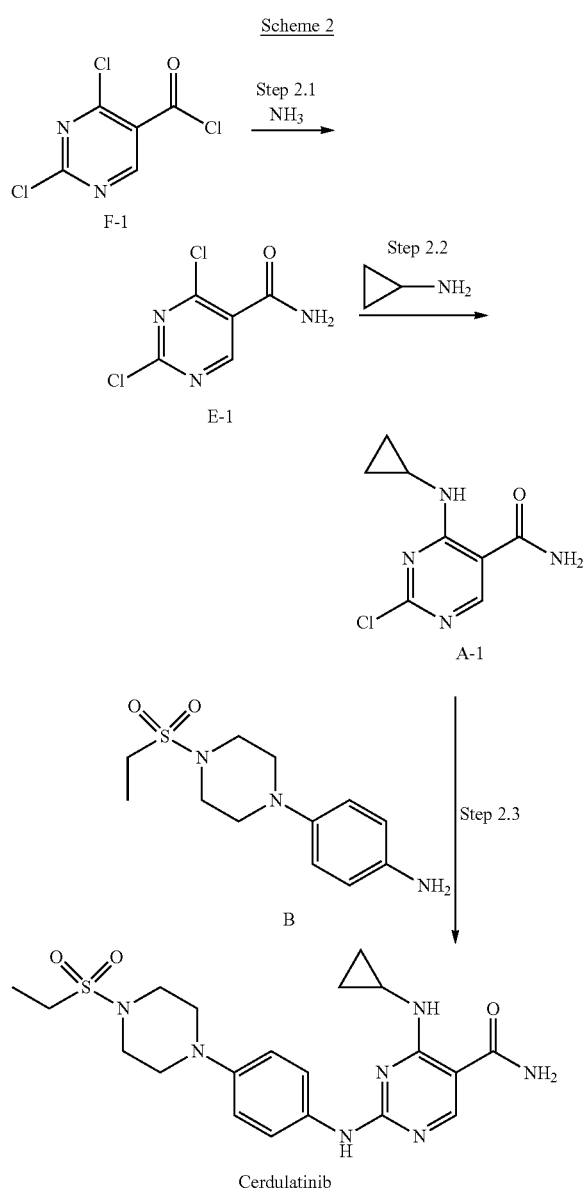

Step 2.1

1.9 to 2.0 equivalents of gaseous ammonia were bubbled into a solution of Compound F-1 in MeTHF in 1 hr at −15° C. or at −5° C. under anhydrous conditions until conversion of Compound F-1 to Compound E-1 completed. The excess of NH₃ was removed with three cycle of vacuum/nitrogen.

Step 2.2

The solution containing Compound E-1 from Step 2.1 was directly engaged in Step 2.2 at −15° C. or −5/0° C. Cyclopropylamine was added in the solution with or without the addition of a base (DIPEA) to obtain Compound A-1.

In one batch, 2.0 equivalents of cyclopropylamine were added to the solution. After 2 hrs of reaction, 0.08% of Compound E-1 was present.

After completion of Step 2.2, the organic phase (MeTHF) was washed with water, which was followed by a solvent swap from MeTHF to NMP to obtain a solution of Compound A-1 in NMP.

Step 2.3

Cerdulatinib was synthesized by addition of Compound B to the NMP solution containing Compound A-1 obtained from Step 2.2 after water wash and solvent swap. In different batches, addition of Compound B was conducted under three different conditions: basic conditions, acidic conditions and neutral conditions.

"Basic Conditions"

Under the basic conditions, 1.0 equivalent of DIPEA was added at the beginning of the reaction at temperatures between 105-110° C., and a reaction time was 12-16 hrs. After isolation, which comprises precipitating cerdulatinib with water, filtration and washing, cerdulatinib was obtained in 69% yield with a purity of about 90%.

"Acid Conditions"

Under the acid conditions, 1.2 equivalents of aqueous HCl was addition at the beginning of the reaction. The reaction proceeded at a temperature of about 80° C. for 6-7 hrs to provide cerdulatinib HCl salt. At the end of reaction, 1.2 equivalents of DIPEA were added, and after isolation, cerdulatinib was obtained with a purity of 93.4% and a yield of 78%.

"Neutral Conditions"

Under the neutral conditions, no acids or bases were added at the beginning of the reaction. The reaction proceeded at 80-90° C. during 8-16 hrs. At the end of the reaction, 1.0 equivalent of DIPEA was added in order to neutralize the HCl generated during the reaction. Cerdulatinib was isolated in a 90% yield with a purity of 91-92%. Alternatively, the reaction was run at 90° C. for 8-12 hrs followed by addition of 1.0 equivalent of TEA. Water was then added and the resulting cerdulatinib precipitation was filtered and washed a mixture of NMP and water, followed by water wash, providing cerdulatinib with purities between 94.7% and 97.9% in average yield of 87%.

Example 3. Preparation of Cerdulatinib HCl Salt

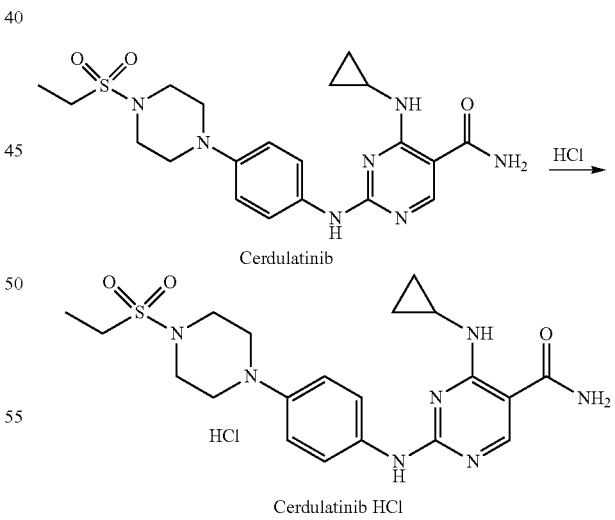

Cerdulatinib was dissolved in DMSO at 75° C. followed by addition of ethanol and 2 equivalents of HCl (1N). The mixture was stirred at 75±5° C. for 12 hrs and then cooled to 20±5° C. The resulting suspension was filtrated and the solid was washed by slurrying in ethanol three times in the reactor, before being dried. Cerdulatinib HCl salt was obtained with a purity of 99.19% and yield of 92%.

Alternative process 1: A 2M HCl solution was prepared in Reactor A (24.82 kg 33% HCl with 112.3 kg water). DMSO (225 kg) and cerdulatinib (50 kg) were added to Reactor B and agitation was started. The Reactor B mixture was heated to 75±5° C. The mixture was agitated until a clear solution was obtained. Ethanol (590 kg) was added to Reactor B and maintained at 75±5° C. until a complete dissolution was observed. 2M HCl was transferred from Reactor A through 1 micron filter cartridge, which caused solid to precipitate. The resulting slurry was agitated at 75±5° C. for at least 30 min, then the mixture was cooled to 15±5° C. The mixture was agitated at 15±5° C. at least 16 hrs. The slurry was filtered through a filter dryer and the wet cake was washed with ethanol (2×240 kg). The cake was dried at 30±5° C. for 12 hrs.

Alternative process 2: A 1M HCl solution was prepared in Reactor A (2 equivalents HCl as 1M HCl in ethanol with 112.3 kg water). DMSO (425 kg) and cerdulatinib (50 kg) were added to Reactor B and agitation was started. The Reactor B mixture was heated to 75±5° C. The mixture was agitated until a clear solution was obtained. Hot ethanol (365 kg) at 75±5° C. was added to Reactor B and maintained at 75±5° C. until a complete dissolution was observed. Over the course of 2 hours, the HCl solution was transferred from Reactor A through 1 micron filter cartridge, which caused solid to precipitate. The resulting slurry was agitated at 75±5° C. for at least 30 min, then the mixture was slowly cooled over the course of 12 hours to 20±5° C. The slurry was filtered through a filter dryer and the wet cake was washed by slurrying three times with ethanol (600 kg), then once in ethanol:water (10:1). The cake was dried at 30±5° C. for 12 hrs at 100 mbar.

Example 4. Alternative Preparation of Cerdulatinib

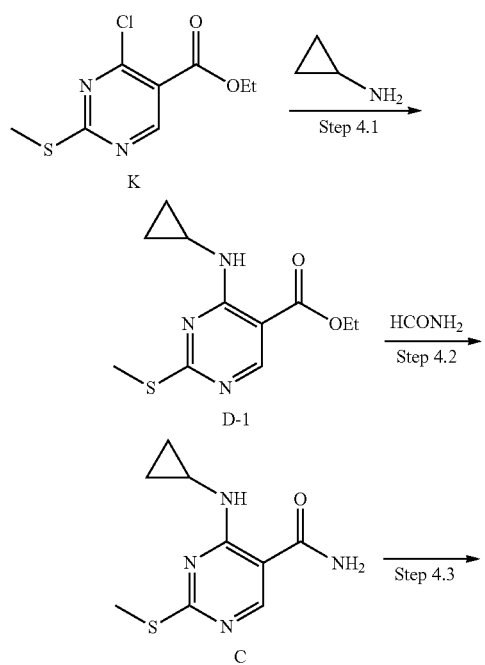

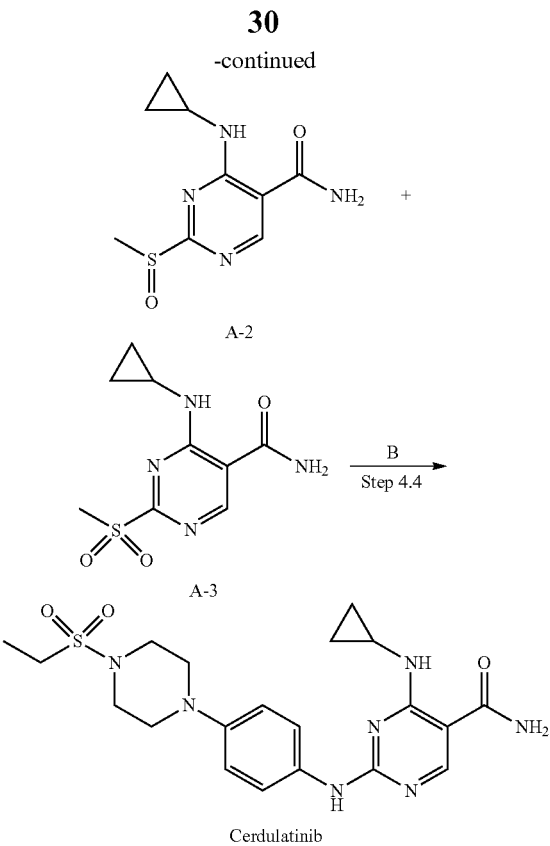

Step 4.1: Conversion of Compound K to Compound D-1

Reactor A was charged with Compound K (37.4 kg), dichloromethane (96.8 kg) and triethylamine (17.1 kg). The mixture was agitated under nitrogen until all solid dissolved (internal temperature 15-30° C.). A solution of cyclopropylamine (9.7 kg) in dichloromethane (13.2 kg) was prepared at room temperature under nitrogen in Reactor B. The solution of cyclopropylamine (9.7 kg) in dichloromethane (13.2 kg) was transferred from Reactor B to Reactor A, resulting in an exothermic reaction. The addition rate was controlled to keep the temperature at <42° C. (addition time ~2 h). A rinse solution of dichloromethane (19.8 kg) was added to Reactor B and then from Reactor B to Reactor A. Internal temperature of Reactor A was maintained at 15-25° C. for 2 h. Water (64.9 kg) was added to Reactor A, with addition rate controlled by temperature (20-30° C.). The mixture in Reactor A was agitated at 20-30° C., then the phases were allowed to separate. The layers were separated and the lower (organic) layer was transferred into Reactor C. The reaction mixture in Reactor C was washed with water (64.9 kg×2). Dichloromethane (19.8 kg) was added to Reactor C, The mixture was distilled to remove dichloromethane. The resulting melted (50° C.) Compound D-1 was filtered.

Step 4.2: Conversion of Compound D-1 to Compound C

Compound D-1 (340 g) was charged into reactor along with THF (680 g), and agitation was started. Agitation continued at 25±5° C. until complete dissolution of materials. Formamide (604 g) was added. The reaction mass was stirred and cooled to 0±5° C. A solution of NaOEt in EtOH (1304 g) was added dropwise while maintaining an internal temperature of 5±5° C. The reaction mixture was stirred at 5±5° C. for 20 h. The reaction mixture was cooled to 0±5° C., then water (6800 g) was added while maintaining the temperature of the reaction mixture at 0±5° C. The suspension was stirred at −5±5° C. for 10 h. The product was filtered using 25 µm industrial web under nitrogen pressure. The filter cake was washed with cooled water (3×374 g), then with MTBE (2×505 mL). The cake was dried at 60° C. with vacuum for 16 h to give Compound C.

Alternate step 4.2: Conversion of Compound D-1 to Compound C

Compound D-1 (340 g) was charged into reactor along with THF (680 g), and agitation was started. Agitation continued at 25±5° C. until complete dissolution of materials. Formamide (604 g) was added. The reaction mass was stirred and cooled to 0±5° C. A solution of NaOEt in EtOH (1304 g) was added dropwise while maintaining an internal temperature of 5±5° C. The reaction mixture was stirred at 5±5° C. for 20 h. The reaction mixture was cooled to 0±5° C., then water (6800 g) was added while maintaining the temperature of the reaction mixture at 0±5° C. The suspension was stirred at −5±5° C. for 10 h. The product was filtered using 25 µm industrial web under nitrogen pressure. The filter cake was washed with water (4×374 g) at 20° C., then once with 2% AcOH in water, then again three times with water, then with MTBE (3×505 mL). The cake was dried at 60° C. with vacuum for 16 h to give Compound C.

Steps 4.3 and 4.4: Conversion of Compound C to Credulatinib

NMP (225 kg) and Compound C were added into Reactor A. The mixture was cooled to 0-5° C. mCPBA (46.2 kg) was then added portion wise, maintaining a temperature of 0-5° C. The loading hopper was rinsed with NMP (5 kg). The reaction mixture was warmed to 25±5° C. The reaction contents were agitated for at least 1 h at 25±5° C. Compound B (37.8 kg) was added and the reaction content was warmed to 45±5° C. The reaction contents were agitated for at least 16 h at 45±5° C. The reaction contents were cooled to 25±5° C. Triethylamine (43.35 kg) was added to make a solution. The reaction contents were warmed to 60±5° C. Water (600 kg) was added slowly, to form a slurry. The reaction contents were cooled to 25±5° C. The reaction contents were agitated for 1 h at 25±5° C. The reaction contents were filtered, then the filter cake was washed with water (255 kg), and EtOH (2×255 kg). The wet cake was slurried in EtOH (255 kg) and the slurry was warmed to 60±5° C. for 0.5 h, then cooled to 25±5° C. The mixture was filtered, then the filter cake was washed with EtOH (255 kg) and the material was dried in a dryer for 12 h at 40±5° C., then cooled to 25±5° C. to give cerdulatinib.

Alternate Steps 4.3 and 4.4: Conversion of Compound C to Credulatinib

NMP (225 kg) and Compound C were added into Reactor A. The mixture was cooled to 0-5° C. mCPBA (46.2 kg) was then added portion wise over 2 hours, maintaining a temperature of less than 10° C. The loading hopper was rinsed with NMP (5 kg). The reaction mixture was warmed to 25±5° C. over the course of 1.5 hours. The reaction contents were agitated for at least 3 h at 25±5° C. Compound B (37.8 kg) was added and the reaction content was warmed to 60±5° C. The reaction contents were agitated for at least 22 h at 60±5° C. The reaction contents were cooled to 25±5° C. Triethylamine (54.19 kg) was added to make a solution. The reaction contents were filtered through a 1 micron carbon filter. The reaction contents were warmed to 60±5° C. Water (600 kg) was added slowly over the course of 3 hours, to form a slurry. The reaction contents were cooled to 25±5° C. The reaction contents were filtered at 25±5° C., then the filter cake was washed with ethanol 8.5 w/w at 25±5° C. (2×255 kg). The wet cake was slurried in THF and the slurry was warmed to 60±5° C. for one hour, then cooled to 25±5° C. The mixture was stirred for one hour. The mixture was filtered, then the filter cake was washed with EtOH (255 kg) and the material was dried in a dryer for 12 h at 40±5° C., then cooled to 25±5° C., to give cerdulatinib.

What is claimed is:

1. A process for preparing Compound A, wherein Compound A is Compound A-2, a salt of Compound A-2, Compound A-3, a salt of Compound A-3, or a mixture thereof:

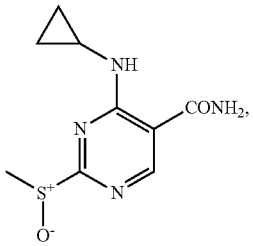

A-2

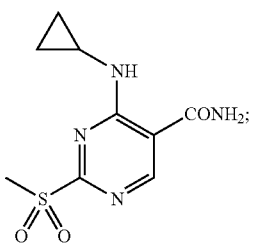

A-3 wherein the process comprises contacting Compound C:

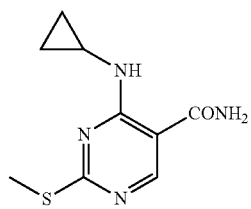

C or a salt thereof with an oxidizing agent;
wherein Compound C is prepared by contacting Compound D-1:

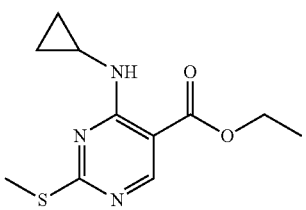

D-1 or a salt thereof with formamide and sodium ethoxide.

2. The process of claim 1, wherein the oxidizing agent is meta-chloroperoxybenzoic acid.

3. The process of claim 1, wherein a molar ratio of the oxidizing agent to Compound C is about 2:1 to about 4:1.

4. The process of claim 1, wherein a molar ratio of the oxidizing agent to Compound C is about 2.5:1 to about 3.5:1.

5. The process of claim 1, wherein a molar ratio of the oxidizing agent to Compound C is about 1.1:1 to about 2:1.

6. The process of claim 1, wherein the contacting of Compound C or the salt thereof with the oxidizing agent is at a temperature of about −10° C. to about 20° C.

7. The process of claim 1, wherein the contacting of Compound C or the salt thereof with the oxidizing agent is in a first solvent.

8. The process of claim 7, wherein the first solvent is N-methylpyrrolidone (NMP).

9. The process of claim 1, wherein Compound D-1 is prepared by a method comprising contacting Compound K

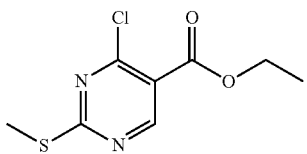

or a salt thereof with cyclopropylamine or a salt thereof to form Compound D-1.

10. The process of claim 1, wherein formamide and Compound D-1 are in a molar ratio of about 5:1 to about 15:1.

11. The process of claim 1, wherein the contacting of Compound D-1 with formamide and sodium ethoxide is in a second solvent.

12. The process of claim 11, wherein the second solvent is THF.

13. The process of claim 1, wherein the contacting of Compound D-1 with formamide and sodium ethoxide is at a temperature of about 0° C. to about 10° C.

14. The process of claim 1, wherein the contacting of Compound D-1 with formamide and sodium ethoxide is for about 10 to about 24 hours.

15. A compound

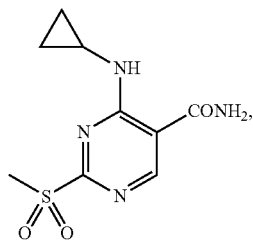 [SMILES: CS(=O)(=O)c1ncc(C(N)=O)c(NC2CC2)n1]

or a salt thereof prepared by the process of claim 1.

* * * * *